(12) United States Patent
Mehta

(10) Patent No.: US 6,669,059 B2
(45) Date of Patent: Dec. 30, 2003

(54) SYSTEM AND METHOD FOR PASSAGE RINSE

(76) Inventor: Ketan C. Mehta, 4077 Polled Hereford Dr., Santa Rosa, CA (US) 95404

(*) Notice: Subject to any disclaimer, the term of this patent is extended or adjusted under 35 U.S.C. 154(b) by 0 days.

(21) Appl. No.: 10/352,723

(22) Filed: Jan. 27, 2003

(65) Prior Publication Data

US 2003/0111491 A1 Jun. 19, 2003

Related U.S. Application Data

(63) Continuation of application No. 09/845,759, filed on Apr. 30, 2001, now Pat. No. 6,520,384.

(51) Int. Cl.[7] .............................................. B65D 37/00
(52) U.S. Cl. ...................................... 222/211; 222/215
(58) Field of Search ........................ 222/207, 211–213, 222/215

(56) References Cited

U.S. PATENT DOCUMENTS

| | | | |
|---|---|---|---|
| 2,571,921 A | 10/1951 | Morris | |
| 2,578,864 A | 12/1951 | Tupper | |
| 2,811,283 A | 10/1957 | Bowen | |

(List continued on next page.)

FOREIGN PATENT DOCUMENTS

| | | |
|---|---|---|
| DE | 296 02 605 U1 | 4/1996 |
| GB | 881807 | 11/1961 |
| WO | WO 96/29044 | 9/1996 |

OTHER PUBLICATIONS

NeilMed, "Sinus Rinse", 2000, London, XP–002207679, p. 7, 14.
Dr. Grossan Sinus Irrigator® Tip. Datasheet [online] Hydro Med Products, Jul. 19, 2000 [retrieved on Apr. 26, 2001]. Retrieved from the Internet: <URL:www.sinus–relief.com/whatsirr.html>.
SinuCleanse® ©2000. Datasheet [online] Med–Systems, Inc. Jan. 27, 2001 [retrieved on Jul. 10, 2001]. Retrieved from the Internet: <URL:www.sinucleanse.com/sinu2.html>.
Sinus–Rinse™ ©2001. Datasheet [online] SINUS–RINSE™ [retrieved on Jul. 10, 2001]. Retrieved from the Internet: <URL:www.sinusrinse.com>.

(List continued on next page.)

Primary Examiner—J. Casimer Jacyna
(74) Attorney, Agent, or Firm—Fish & Richardson P.C.

(57) ABSTRACT

An apparatus and method for preparing a pH balanced saline solution and using the saline solution for rinsing a nasal passage. The apparatus includes a container having flexible sidewalls and an opening for a removable cap. The cap has a rounded convex upper portion curving away from an opening at the cap's uppermost surface and has a conduit in the cap's interior, which conduit extends into the container when the apparatus is fully assembled or is connected to a tube that extends in the container. A saline solution is prepared by adding sodium chloride and sodium bicarbonate to distilled water. The sidewalls of the container, filled with the saline solution, are compressed to urge the saline solution through the conduit, or tube and conduit, and through the opening in the cap and into a nasal passage, the cap being pressed against a nostril to provide a comfortable and effective seal.

38 Claims, 4 Drawing Sheets

U.S. PATENT DOCUMENTS

| | | | |
|---|---|---|---|
| 3,363,808 A | * 1/1968 | Gorman | 222/633 |
| 3,847,145 A | 11/1974 | Grossan | |
| 4,083,840 A | * 4/1978 | Schoefberger | 534/797 |
| 4,356,941 A | 11/1982 | McRoskey | |
| 4,439,206 A | * 3/1984 | Hildebrand et al. | 8/543 |
| 4,489,535 A | 12/1984 | Veltman | |
| 4,513,891 A | 4/1985 | Hain et al. | |
| 4,555,469 A | * 11/1985 | Erdmann et al. | 430/168 |
| 4,925,128 A | 5/1990 | Brody | |
| 5,316,054 A | 5/1994 | Hall et al. | |
| 5,354,849 A | * 10/1994 | Schoefberger | 534/637 |
| 5,806,723 A | 9/1998 | DuBose | |
| 5,897,872 A | 4/1999 | Picciano | |
| 5,899,878 A | 5/1999 | Glassman | |
| 5,967,377 A | * 10/1999 | Glynn | 222/158 |
| 6,293,436 B2 | * 9/2001 | Faughnder et al. | 222/211 |

OTHER PUBLICATIONS

Using the Pulsatile Nasal Irrigator. Datasheet [online] Hydro Med Inc. Aug. 7, 2000 [retrieved on Apr. 27, 2001]. Retrieved from the Internet: <URL:www.ent–consult.com/nasal irr use.html>.

Breathe Ease ©2000. Datasheet [online] Hydro Med Inc. Apr. 16, 2000. 6 pages.

Entso®, Datasheet [online], Retrieved from the Internet: <URL: www.entsolwash.com>. [undated; pre–April 30, 2001].

"RhinoCare® Nasal Douche" brochure, Siemens & Co. (5 pages. English translation 12 pages.) (pre–Apr. 30, 2001).

Tomooka, Lance T., et al., "Clinical Study and Literature Review of Nasal Irrigation" *The Laryngoscope*, ©2000 The American Laryngological, Rhinological and Otological Society, Inc. pp. 1189–1193, Jul. 2000.

Got a medical concern?—Ethicare—Nasal Irrigators™ 2001, Datasheet [online] Ethicare, Jan. 11, 2001, retrieved from the Internet: <URL www.ethicare.com>.

Rhinotip Irrigation Regimen ©2000, 1999. Datasheet [online] Comtech Solutions. Retrieved from the Internet: www.sinushealth.com.

* cited by examiner

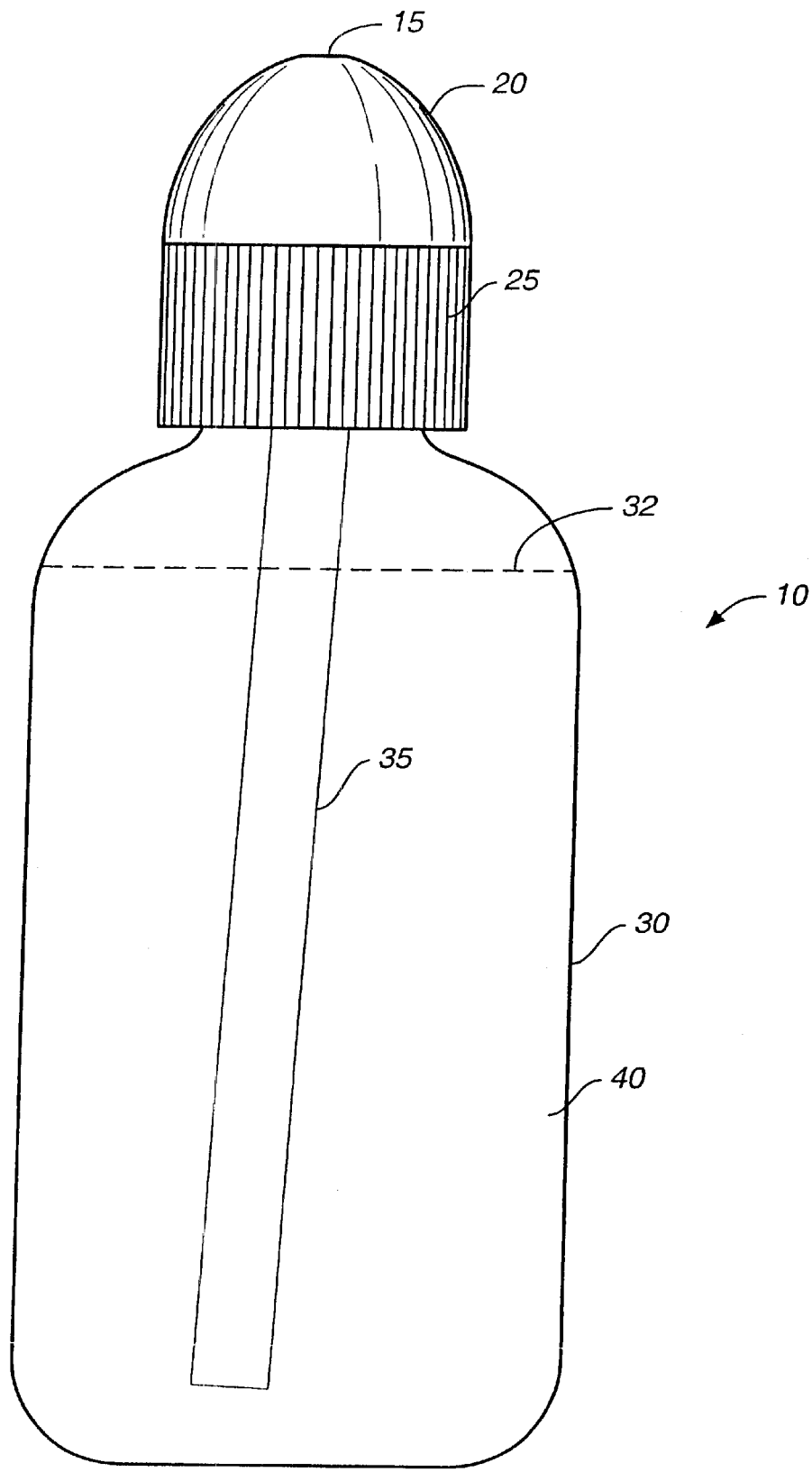
FIG._1

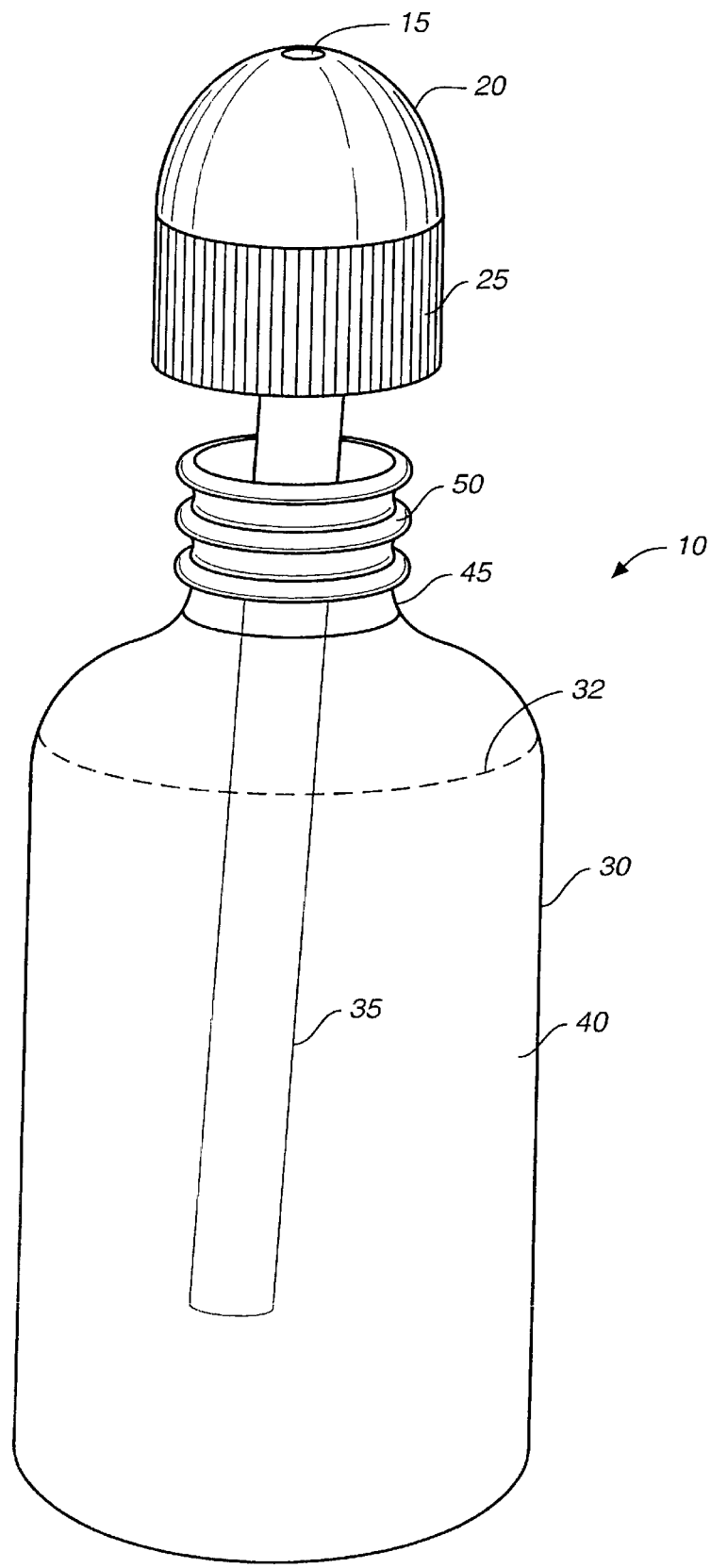
FIG._2

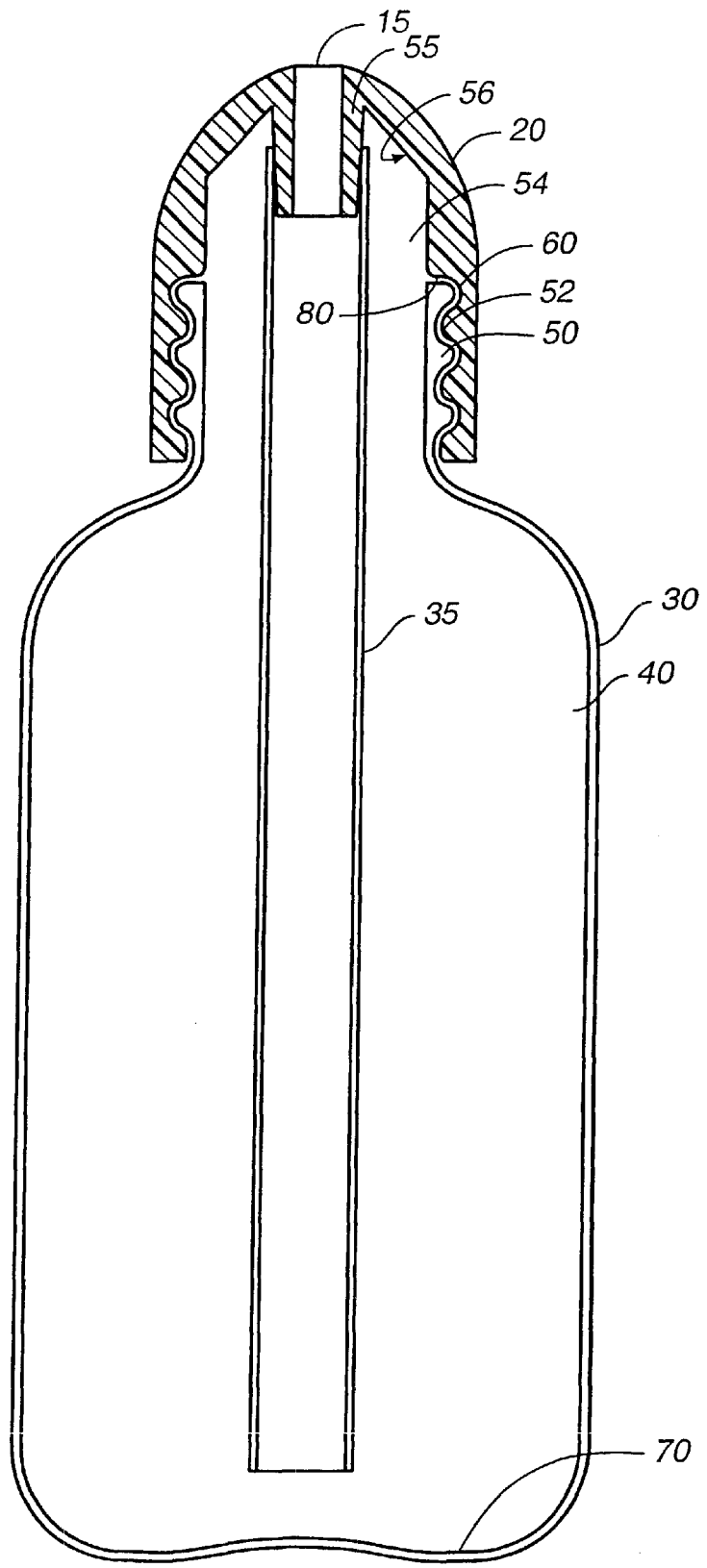
FIG._3

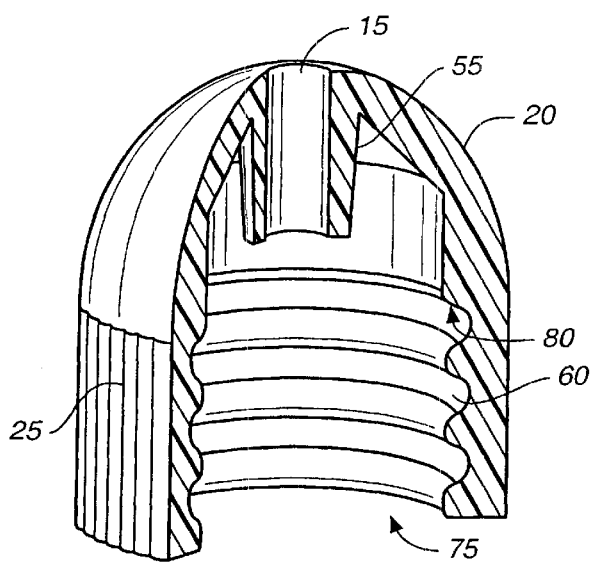
FIG._4
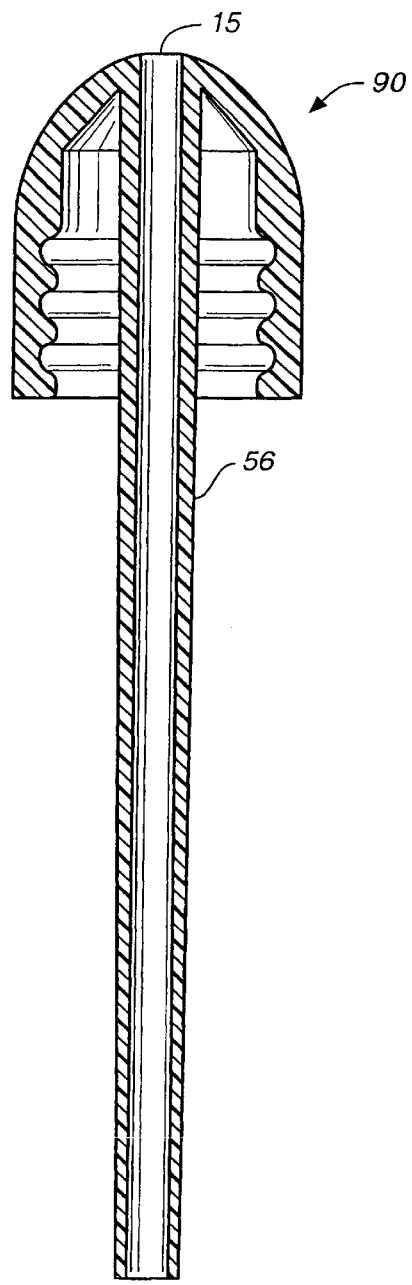
FIG._5

SYSTEM AND METHOD FOR PASSAGE RINSE

CROSS-REFERENCE TO RELATED APPLICATIONS

This application is a continuation application of and claims priority to U.S. application Ser. No. 09/845,759, now U.S. Pat. No. 6,520,384, filed on Apr. 30, 2001, the entirety of which is incorporated herein by reference.

BACKGROUND

A sinus is a hollow space within the bones of the face. Humans have several sinuses. The sinuses are lined with delicate membrane called mucosa. The sinuses humidify and warm the air, add to the sense of smell and play a significant role in the quality of human sound. A nasal passage runs from the nostrils to the pharynx and is also lined with mucosa. Sinusitis is an inflammation of the mucosa of various sinuses, which are located around the nasal passages. Rhinitis is an inflammation of the mucosa of a nasal passage.

Sinusitis and rhinitis can be caused by cold viruses, allergies to various allergens, smoking, bacterial or fungal infections, nasal polyps, deviated nasal septums and non-allergic hypersensitivities. Symptoms of rhinitis include: stuffy nose, runny or drippy nose, scratchy throat and dry cough. Symptoms of sinusitis are more severe than the symptoms of rhinitis. Acute and chronic sinusitis occurs when the sinuses are inflamed and ostia are blocked. Symptoms include: nasal congestion; runny or stuffy nose; white, yellow or green discharge; headache; night time cough; pain in the upper jaw or teeth; persistent fatigue; fever; loss of sense of smell or taste; and sometimes serious infections like meningitis, brain abscess or ear infections.

As indicated above, allergies can cause rhinitis and sinusitis. Allergens are organic particles that attach to the nasal mucosa or respiratory mucosa and lead to the development of an antibody, which subsequently creates a series of chemical reactions leading to symptoms. Every individual's reaction to allergen exposure is different. Indoor allergens including dust mites, mold, pet dander and cockroaches. Outdoor allergens including pollens, grass and mold. Other substances such as cigarette smoke, perfumes and aerosol sprays are irritants that can worsen allergy and sinus symptoms.

There are various methods to treat the symptoms of or to cure sinus disease, including surgery. An effective nasal rinse can significantly reduce or permanently cure the symptoms of nasal allergies and sinus disease. Saline nasal irrigations have been used for many years and have been mentioned in medical textbooks going back hundreds of years. A wide variety of techniques have been described, including swimming in salt water, which often results in some degree of inadvertent nasal salt water irrigation.

Nasal rinsing or lavage is a treatment for rhinitis and sinusitis that uses a saline solution dispensed into the nasal passage to cleanse and wash away mucus and allergy creating particles and irritants. Lavaging allows the sinuses to drain normally and reduces the inflammation of the mucus membrane.

Prepared saline solution is available for uses including nasal lavage, however a bottle filled with saline solution can be quite expensive. Alternatively, saline solution can be prepared at home using household ingredients. However, there is a concern for cleanliness and contamination and for ensuring the proper concentration level and acidity is achieved. Thus, there is a need for a simple method for preparing a saline solution having a consistent and appropriate concentration that is simple, inexpensive and not easily contaminated.

Nasal rinsing equipment currently available includes various types of dispensers that can be filled with a saline solution and which are then injected into the user's nasal passage. Conventional nasal rinsing equipment can be crude and may only be suitable for user's having a certain size nostril. For proper use, the dispensing tip should comfortably seal against a user's nostril. Equipment having a dispenser tip designed for a certain size nostril can be useless for someone with a smaller nostril, in particular children, such as the nasal rinse equipment described in U.S. Pat. No. 5,806,723 for a DEVICE FOR LAVAGING. Thus, there is a need for equipment having a dispenser tip that effectively and comfortably seals against human nostrils of varying sizes, including nostrils of children.

Another problem with current lavaging equipment is that the configuration of the dispensing tip can cause the saline solution to be dispensed into the nasal passage without sufficiently dispersing before reaching the back of the nasal passage, resulting in an uncomfortable or painful sensation for the user. There is a need for a dispenser tip configured to allow the saline solution to disperse sufficiently before reaching the back of the nasal passage.

Conventional lavaging equipment includes dispenser tips that are compatible with power operated oral irrigators. However, the dispenser tips are typically only compatible with a certain model of oral irrigator, such as the dispenser tip described in U.S. Pat. No. 3,847,145 for a NASAL IRRIGATION SYSTEM. There is a need for a dispenser tip that is compatible with most commercially available oral irrigators.

For the foregoing reasons, there is a need for an apparatus and system for preparing and dispensing a saline solution that is simple to use, capable of being prepared and administered in most any location, relatively inexpensive and suitable for use by persons having nostrils of varying sizes, including children.

SUMMARY

The present invention is directed to an apparatus and method for preparing and dispensing a saline solution into a nasal passage. An apparatus for dispensing a liquid into a human nostril comprises a container and a removable cap. The cap has a cylindrical lower portion, a rounded convex upper portion curving away from an axially aligned opening located in the uppermost surface of the upper portion, an open lower end and a tubular conduit connected to the uppermost interior surface of the upper portion and having a hollow center axially aligned with the opening located in the upper portion. The container has flexible sidewalls and an axially aligned neck configured to connect to the cap with a liquid tight connection. The conduit of the cap can extend into the container when the cap and container are joined together, or a flexible tube can be connected to the conduit, which flexible tube extends into the container.

The saline solution comprises sodium chloride and sodium bicarbonate dissolved in water to form an isotonic and pH balanced solution. The water can be distilled and lukewarm.

A method for rinsing a nasal passage comprises preparing the saline solution by emptying the contents of a packet containing a measured amount of sodium chloride and sodium bicarbonate into a container filled with a measured amount of water and dissolving the sodium chloride and sodium bicarbonate in the water, connecting the cap and tube assembly (or cap having an extended conduit) to the container, pressing the cap against a nostril for an effective seal, and compressing the sidewalls of the container to urge the saline solution out of the container and into a nasal passage through the nostril.

Another aspect of the invention includes connecting the cap and tube (or cap having an extended conduit) to a power operated oral irrigator having a reservoir containing the saline solution and operating the oral irrigator to drive the saline solution into a nasal passage.

Advantages of the invention include one or more of the following. A nasal rinse apparatus is provided that can be used by children as well as adults. The apparatus includes a cap design that will provide an effective seal against the nostril of a child or adult.

The cap can be used in conjunction with a power driven oral irrigator for performing a nasal rinse. A flexible tube is provided that can be connected to most commercially available oral irrigators.

A nasal rinse can be performed without having to bend the neck back and look upwards, as is the case in nasal irrigation systems that rely on gravity to dispense the solution. This feature is particularly advantageous to persons who experience dizziness in this position, in particular elderly persons.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a side view of a dispenser assembly.

FIG. 2 is a side view of the dispenser assembly of FIG. 1 with the cap partially removed.

FIG. 3 is a cross-sectional view of the dispenser assembly of FIG. 1.

FIG. 4 is a cross-sectional view of the cap of FIG. 1.

FIG. 5 is a cross-sectional view of a cap with an extended conduit.

Like reference symbols in the various drawings indicate like elements.

DETAILED DESCRIPTION

Referring now to FIG. 1, an apparatus for performing a nasal rinse using a saline solution is shown. A dispenser assembly 10 includes a container 30, a cap 20 and a tube 35 connected to the interior portion of the cap 20 and extended into the container 30. The cap 20 can be removed from the container 30 by rotating the cap 20 (e.g., counter-clockwise), to allow the container 30 to be filled with a saline solution 40.

Referring now to FIGS. 2 through 4, the apparatus will be described in greater detail. The container 30 has flexible sidewalls that can be easily compressed by a hand to force the saline solution 40 through the tube 35 and through an opening 15 at the top of the cap 20, when the cap 20 is secured to the container 30. The uppermost portion of the container 30 includes a neck 45 that can include threads 50 to provide a tight connection to the cap 20 to prevent the escape of saline solution 40. However, attachment of cap 20 to container 30 can be accomplished in any convenient fashion that allows for removability and which maintains a liquid tight seal. Other methods for attachment can include a ring and groove assembly, a compression-fitting cap, exterior clamps or the like. The container 30 can include a marking 32 to indicate a liquid level. The marking 32 can be in any convenient form such as a printed line, a groove, a ring or the like. The container 30 can be made of a transparent material, such as a low-density polypropylene, so the amount of saline solution 40 is visible and the container 30 can be inspected for cleanliness. The container 30 should be able to withstand the heat of lukewarm to hot water and should be microwave safe to allow convenient heating of the contents of the container 30.

The cap 20 is hollow. The exterior of cap 20 has a cylindrically shaped lower portion and a conically shaped upper portion. The cap 20 has a lower opening 75 to secure cap 20 onto container 30 and an upper opening 15 at the apex of the conically shaped upper portion for expulsion of the saline solution 40 from the cap 20. The cylindrical lower portion of the exterior surface of cap 20 can include rounded, vertical ridges 25 to allow a user to grip the cap 20 when either securing the cap 20 onto, or removing the cap 20 from, the neck 45 of the container 30. The conical upper portion of the exterior surface of cap 20 includes a smooth finish to allow a comfortable and effective seal against a user's nostril.

The exterior of the conical upper portion of cap 20 immediately slopes downward from opening 15 to the ridges 25. The exterior shape of a longitudinal cross-section of the upper portion of cap 20 can be a curve formed by the combination of at least three arcs. The uppermost portion of the curve can be an arc that is a portion of a circle having a first radius and the side portions of the curve can be arcs that are portions of a circle having a second radius. In the example of a cap 20 having a total height of approximately 40 mm and an exterior diameter at its widest point of approximately 29 mm, the first radius is approximately 10 mm and the second radius is approximately 30 mm. In another implementation, the exterior shape of a longitudinal cross-section of the upper portion of cap can be elliptical.

The conical shape of the upper portion of cap 20 allows the cap 20 to be inserted into and sealed against the nostril of either a child or an adult, even though an adult typically has a relatively larger nostril. In the case of an adult, the cap 20 is inserted slightly further into the nasal passage before an effective seal is achieved.

The interior of cap 20 can form a first cylinder 52 extending from the lower surface of cap 20 to a height approximately one half of the total height of cap 20. The surface of approximately the lower quarter of the first cylinder 52 is smooth and the surface of the remainder of the first cylinder 52 can have threads 60 to permit a tight, threaded connection to the neck 45 of the container 30. The interior of cap 20 can form a second cylinder 54 extending from the top of the first cylinder 52 to a height approximately one quarter of the total height of cap 20. The second cylinder 54 has a smaller diameter than the first cylinder 54, thereby forming a lower surface 80 of the second cylinder 54, which lower surface 80 abuts the upper surface of the neck 45 of the container 30 when the cap 20 is secured onto container 30. The interior of cap 20 further forms a cavity having interior walls 56 slanting or curving from the top of the second cylinder 54 to the top of the exterior of a conduit 55 extending vertically downwards from opening 15.

The opening 15 leads into a conduit 55 that extends vertically from opening 15 downwards into the interior of cap 20. The exterior diameter of the conduit 55 gradually tapers from the diameter at the top of conduit 55 (closest to opening 15) to a lesser diameter at the bottom of conduit 55. The interior diameter remains substantially constant the entire length of the conduit 55. The tapered exterior of conduit 55 allows tube 35 to be forced over the top of the exterior of conduit 55 to form a snug fit. However, attachment of tube 35 to conduit 55 can be accomplished in any convenient fashion, including the addition of a ring (not shown) around the exterior of conduit 55 to effectively lock tube 35 onto conduit 55 once tube 35 is forced over the ring.

The diameter of opening 15 affects the flow rate of the saline solution 40 out of the cap 20. If the opening 15 is too small, the saline solution 40 will enter a user's nasal passage at such a velocity that the stream of saline solution 40 will not sufficiently disperse before reaching the rear wall of the user's nasal cavity and the force at which the saline solution 40 impacts the rear wall of the user's nasal cavity will cause a jabbing sensation. If the opening 15 is too large, the saline solution 40 will not exit the cap 20 with enough force to reach the rear wall of a user's nasal cavity. In one implementation, the diameter of opening 15 is made to be no larger than approximately 4.25 mm and no smaller than approximately 2.5 mm to allow the saline solution 40 to exit the cap 20 with enough force both to fully irrigate the nasal passage and to sufficiently disperse before reaching the rear wall of the user's nasal cavity to minimize any user discomfort. The conical shape of the upper portion of cap 20 allows an effective seal to be formed against a nostril being at least as large as the opening 15. The diameter of opening 15 is sized such that an effective seal can be formed against the nostril of a child as well as an adult.

The cap 20 can be constructed from a rigid plastic such as low-density polypropylene. Alternatively, cap 20 can be constructed from any other non-toxic rigid substance, including stainless steel. The cap 20 can be approximately 40 mm in height and have an exterior diameter at its widest point of approximately 29 mm.

When dispenser assembly 10 is fully assembled, tube 35 is connected to conduit 55 and cap 20 is secured to container 30. Tube 35 extends into the interior of container 30, the lower surface of tube 35 being approximately half an inch above the base 70 of container 30. The tube can be made of a latex free, non-toxic, strong and flexible material such as polyurethane.

Referring now to FIG. 5, in another implementation, the cap and tube assembly can be a single unit. Cap 90 is similar in shape to cap 20, but modified such that conduit 56 extends a length comparable to the length of tube 35. The cap 90 can be made of a rigid plastic such as a low density polyethylene. Cap 90 can be connected to container 30 in the same manner as described above with reference to cap 20.

The dispenser assembly 10 can also include a plug or stopper (not shown) that fits into conduit 55 or conduit 56 through opening 15, to retain the saline solution 40 in the container 30 to permit transporting of the dispenser assembly 10 without leakage of the saline solution 40. The connection of the plug to cap 20 or cap 90 could be by any convenient means including a compression-fit or threaded connection.

The saline solution 40 can be prepared by dissolving sodium chloride (NaCl) and sodium bicarbonate (NaHCO$_3$) in water. Preferably distilled water is used, but purified or clean tap water can also be used. Packets containing a mixture of NaCl and NaHCO$_3$ for preparing a pH balanced, isotonic saline solution are available from NeilMed™ Products located in Santa Rosa, Calif. One size packet available contains an approximately 2.16 gram mixture of approximately 39 parts NaCl and 1 to 2 parts NaHCO$_3$, and can be used to prepare an isotonic saline solution having a concentration of approximately 0.9% to 1%, by dissolving the contents of the packet into 8 ounces of distilled water. A hypertonic saline solution can be prepared by dissolving two or three packets of the NaCl/NaHCO$_3$ mixture in 8 ounces of distilled water. The packets contain all natural and iodine free ingredients to form a pH balanced, isotonic saline solution that is compatible with the human nasal and sinus mucosa to prevent burning or stinging during nasal lavage, which negative sensations could be caused by a saline solution prepared using home ingredients, such as table salt. Preparing a saline solution using only table salt, and therefore without NaHCO$_3$, results in a more acidic solution that can cause burning when used to a rinse a nasal passage. An aluminum lining can be used inside the packets to protect the contents from moisture, which can adversely affect the ease with which the NaCl/NaHCO$_3$ dissolves in the water. A dotted line is marked on the exterior of the packet to provide a guide for cutting open the packet.

The dispenser assembly 10 and saline solution 40 can be used to perform a nasal rinse. Using the method described below, a user of the dispenser assembly 10 can irrigate the nasal passage to removed mucus, allergens and irritants. Starting with the cap 20 removed from the container 30, the container 30 is filled with eight ounces of distilled water. A dashed line marked on the exterior of container 30 indicates to a user when eight ounces of fluid has been poured into the container 30. The water can then be warmed in a microwave oven. It is recommended to warm the water using five second increments to avoid excessive heating. If the water is heated to hotter than lukewarm, it is recommended to allow the water to cool before proceeding. Alternatively, the water can be warmed before pouring it into container 30 or does not have to be warmed at all.

A packet containing the NaCl/NaHCO$_3$ mixture is cut open along the dotted line and emptied into the container 30. The cap 20 having the tube 35 connected to the conduit 55 is secured onto the container 30 by aligning the threads 60 of cap 20 with the threads 50 of neck 45 and screwing the cap 20 onto the neck 45 by gripping the ridges 25 and rotating the cap 20 clockwise until fully tightened. The dispenser assembly 10 is shaken until the NaCl/NaHCO$_3$ mixture is fully dissolved in the distilled water.

The user bends forward to a comfortable level, tilting the head slightly down and applies the cap 20 snugly against the left nostril with opening 15 directed into the left nasal passage. The container 30 is squeezed to force the saline solution 40 to enter the left nasal passage. The process is repeated applying the cap snugly against the right nostril. The saline solution 40 that was injected into the nasal passages will drain from the nasal passages or the mouth and should not be swallowed by the user. The user then gently blows the nose. Any unused portion of the saline solution 40 is discarded and the dispenser assembly 10 is cleaned. A nasal rinse can be performed once or twice a day or as recommended by a qualified physician.

The cap 20, tube 35 and container 30 should be thoroughly cleaned after each nasal rinse usage. The cap 20 can be sterilized by submersing it briefly in boiling water. The tube can be cleaned by rinsing the tube thoroughly with water and using a narrow brush to clean the interior, such as the type of brush commercially available for cleaning baby bottles. The container 30 can similarly be cleaned by rinsing the container 30 with water and using an appropriately-sized brush. A vinegar and water solution can also be used to clean the dispenser assembly 10.

An alternative ravaging technique includes using a power operated water jet dispenser designed for oral irrigation attached to a dispenser tip suitable for nasal irrigation. An oral irrigator such as the Waterpik® Oral Irrigator manufactured by The Waterpik Technologies Personal Healthcare Products Division of Water Pik Technologies, Inc., based in Fort Collins, Colo., can be used in conjunction with cap 20 and tube 35 to perform a nasal lavage. Tube 35 has an inner diameter such that it can form a snug fit connection to a water tube (not shown) forming part of the oral irrigator. The flexibility of tube 35 permits compatibility to most commercially available oral irrigators. The water reservoir element of the oral irrigator is filled with a saline solution that can be prepared using the method described above. The oral irrigator can then be operated to drive the saline solution through the water tube into tube 35 and out of opening 15 into a user's nasal passage.

Cap 90 can also be used in conjunction with an oral irrigator as described above. A length of flexible tubing (not shown) can be used as a coupling between conduit 56 and a water tube forming part of the oral irrigator.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus for dispensing liquid, the apparatus comprising:
    a cap having:
        a cylindrical lower portion having a substantially constant exterior diameter and capable of attaching to a liquid container;
        a rounded convex upper portion curving away from an axially aligned opening from which a liquid is dispensed located in the uppermost surface of the upper portion and curving downwardly toward and smoothly transitioning into the cylindrical lower portion, the upper portion and the lower portion having substantially the same exterior diameter at the point of transition;
        an open lower end; and
        a tubular conduit connected to the uppermost interior surface of the upper portion and having a hollow center axially aligned with the opening located in the upper portion.

2. The apparatus of claim 1, wherein the exterior surface of the lower portion comprises a plurality of rounded, vertical ridges.

3. The apparatus of claim 1, wherein the diameter of the opening is no smaller than 2.5 mm and no greater than 4.25 mm.

4. The apparatus of claim 1, wherein the conduit has a slightly decreasing exterior diameter from the top of the conduit to the bottom.

5. The apparatus of claim 1, further comprising:
    a tube connected to the conduit.

6. The apparatus of claim 5, wherein the tube is connected to the conduit using a snug fit connection.

7. The apparatus of claim 5, further comprising:
    a container having flexible sidewalls and an axially aligned neck having an open end, wherein the lower portion of the cap and the neck of the container are configured to join together with a liquid tight connection.

8. The apparatus of claim 7, wherein the liquid tight connection is a threaded connection.

9. The apparatus of claim 7, further comprising:
    a marking on the container for indicating a liquid level.

10. The apparatus of claim 7, wherein the container is made of a transparent material.

11. The apparatus of claim 1, further comprising:
    a container having flexible sidewalls and an axially aligned neck having an open end, wherein the lower portion of the cap and the neck of the container are configured to join together with a liquid tight connection.

12. The apparatus of claim 11, wherein the liquid tight connection is a threaded connection.

13. The apparatus of claim 11, further comprising:
    a marking on the container for indicating a liquid level.

14. The apparatus of claim 11, wherein the container is made of a transparent material.

15. A system comprising:
    a pH balanced, iodine-free saline solution having a concentration in the range of approximately 0.9% to 1% comprised of approximately 39 parts sodium chloride and approximately 1 to 2 parts sodium bicarbonate dissolved in water; and
    an apparatus for dispensing the saline solution, the apparatus comprising:
        a cap having:
            a cylindrical lower portion,
            a rounded convex upper portion curving away from an axially aligned opening from which a liquid is dispensed located in the uppermost surface of the upper portion and curving downwardly to join the cylindrical lower portion, an open lower end, and
            a tubular conduit connected to the uppermost interior surface of the upper portion, the conduit having a hollow center axially aligned with the opening located in the upper portion; and
        a container for holding the saline solution, the container having flexible sidewalls and an axially aligned neck having an open end, wherein the lower portion of the cap and the neck of the container are configured to join together with a liquid tight connection.

16. The system of claim 15, wherein:
    the saline solution is dispensed into a nasal passage; and
    the cap is configured to provide a seal against a human nostril at least as large the opening in the cap.

17. The system of claim 15 wherein:
    the saline solution is isotonic and lukewarm.

18. The system of claim 15, wherein the exterior surface of the lower portion of the cap comprises a plurality of rounded, vertical ridges.

19. The system of claim 15, wherein the diameter of the opening in the cap is no smaller than 2.5 mm and no greater than 4.25 mm.

20. The system of claim 15, wherein the conduit has a slightly decreasing exterior diameter from the top of the conduit to the bottom.

21. The system of claim 15 wherein the liquid tight connection is a threaded connection.

22. The system of claim 15, further comprising:
    a marking on the container for indicating a liquid level.

23. The system of claim 15, wherein the container is made of a transparent material.

24. The system of claim 15, wherein the apparatus further comprises:
    a tube for transporting the saline solution from the container through the opening in the cap when the sidewalls of the container are compressed the tube connected to the conduit.

25. The system of claim 24, wherein:
the saline solution is isotonic and lukewarm.

26. The system of claim 24, wherein the exterior surface of the lower portion of the cap comprises a plurality of rounded, vertical ridges.

27. The system of claim 24, wherein the diameter of the opening in the cap is no smaller than 2.5 mm and no greater than 4.25 mm.

28. The system of claim 24, wherein the conduit has a slightly decreasing exterior diameter from the top of the conduit to the bottom.

29. The system of claim 24, wherein the liquid tight connection is a threaded connection.

30. The system of claim 24, further comprising:
a marking on the container for indicating a liquid level.

31. The system of claim 24, wherein the container is made of a transparent material.

32. A system comprising:
a mixture comprised of approximately 39 parts sodium chloride and approximately 1 to 2 parts sodium bicarbonate dissolved in water to form a pH balanced, iodine-free saline solution having a concentration in the range of approximately 0.9% to 1%; and
an apparatus for dispensing the saline solution.

33. The system of claim 32, the apparatus including:
a cap having:
a cylindrical lower portion,
a rounded convex upper portion curving away from an axially aligned opening from which a liquid is dispensed located in the uppermost surface of the upper portion and curving downwardly to join the cylindrical lower portion,
an open lower end, and
a tubular conduit connected to the uppermost interior surface of the upper portion, the conduit having a hollow center axially aligned with the opening located in the upper portion;
a power operated oral irrigator having a reservoir containing the saline solution; and
a tube having two ends, wherein the first end is connected to the conduit and the second end is connected to the oral irrigator.

34. The system of claim 33, wherein the saline solution is dispensed into a nasal passage and the cap is configured to provide a seal against a human nostril.

35. A method for rinsing a passage, the method comprising:
preparing a pH balanced, iodine-free saline solution having a concentration in the range of approximately 0.9% to 1% by emptying the contents of a packet containing a measured amount of sodium chloride and sodium bicarbonate, the amount being approximately 39 parts sodium chloride and approximately 1 to 2 parts sodium bicarbonate, into a container filled with a measured amount of water and dissolving the sodium chloride and sodium bicarbonate in the water, wherein the container has flexible sidewalls;
connecting a cap the container with a liquid tight connection, the cap having:
a cylindrical lower portion,
a rounded convex upper portion curving away from an axially aligned opening from which a liquid is dispensed located in the uppermost surface of the upper portion and curving downwardly to join the cylindrical lower portion,
an open lower end, and
a tubular conduit connected to the uppermost interior surface of the upper portion and having a hollow center axially aligned with the opening located in the upper portion and wherein the conduit extends into the container or the conduit is connected to a tube extending into the container with a snug fit connection; and
compressing the sidewalls of the container to urge the saline solution out of the container and into the passage.

36. The method of claim 35, wherein the passage is a nasal passage and the cap is configured to provide a seal against a nostril, the method further comprising:
pressing the cap against a nostril for an effective seal.

37. A method for rinsing a passage, the method comprising:
preparing a pH balanced, iodine-free saline solution having a concentration in the range of approximately 0.9% to 1% by mixing a measured amount of sodium chloride and sodium bicarbonate, the amount being approximately 39 parts sodium chloride and approximately 1 to 2 parts sodium bicarbonate, with a measured amount of distilled water and dissolving the sodium chloride and sodium bicarbonate in the distilled water; and
dispensing the saline solution into a passage to rinse the passage.

38. The method of claim 37, wherein the passage is a nasal passage.

* * * * *